United States Patent
Deflorian et al.

(10) Patent No.: US 8,881,941 B2
(45) Date of Patent: Nov. 11, 2014

(54) EVAPORATOR DEVICE FOR VOLATILE SUBSTANCES

(75) Inventors: Stefano Deflorian, Trento (IT); Walter Sordo, Trento (IT); Franco Zobele, Trento (IT)

(73) Assignee: Zobele Holding S.p.A., Trento (IT)

( * ) Notice: Subject to any disclaimer, the term of this patent is extended or adjusted under 35 U.S.C. 154(b) by 749 days.

(21) Appl. No.: 11/925,096

(22) Filed: Oct. 26, 2007

(65) Prior Publication Data

US 2008/0099575 A1    May 1, 2008

Related U.S. Application Data

(60) Provisional application No. 60/863,051, filed on Oct. 26, 2006.

(51) Int. Cl.
*B65D 43/18* (2006.01)
*A01M 1/20* (2006.01)
*A61L 9/03* (2006.01)

(52) U.S. Cl.
CPC .............. *A01M 1/2077* (2013.01); *A61L 9/03* (2013.01)
USPC ........... 220/813; 220/811; 220/833; 220/836; 392/390; 392/403; 392/406; 239/51.5; 239/57; 239/302

(58) Field of Classification Search
USPC ............... 239/34, 47, 51.5, 57–59, 302, 326; 222/325; 220/810, 811, 813, 833, 836; 392/390, 392, 394, 395, 403, 404, 406
See application file for complete search history.

(56) References Cited

U.S. PATENT DOCUMENTS

| | | | | |
|---|---|---|---|---|
| 2,611,068 A * | 9/1952 | Wellens | ......................... | 392/392 |
| 4,523,870 A | 6/1985 | Spector | | |
| 4,675,504 A * | 6/1987 | Suhajda | ......................... | 392/390 |
| 4,804,821 A * | 2/1989 | Glucksman | .................... | 392/390 |
| 4,849,606 A * | 7/1989 | Martens et al. | ................ | 392/390 |
| 6,085,989 A | 7/2000 | Cox | | |
| 6,241,161 B1 | 6/2001 | Corbett | | |

FOREIGN PATENT DOCUMENTS

| | | |
|---|---|---|
| EP | 1 547 464 | 6/2005 |
| JP | 2004-267197 | 9/2004 |
| WO | WO 01/68154 | 9/2001 |
| WO | WO 02/07511 | 1/2002 |

OTHER PUBLICATIONS

International Search Report mailed on Feb. 8, 2008 in corresponding International Application No. PCT/EP2007/061387.

* cited by examiner

*Primary Examiner* — Jason Boeckmann
(74) *Attorney, Agent, or Firm* — Ostrolenk Faber LLP

(57) ABSTRACT

The present invention refers to an evaporator device for volatile substances provided with a closure system that facilitates the replacement of the refill or container of the volatile substance. The invention provides a safety closure system for the evaporator device, which makes difficult for children to get access to the tablet or container of the volatile substance. A closure member and a container are associated in such a manner that during the opening movement of the closure member, at least part of the container is extracted out of the chamber.

4 Claims, 8 Drawing Sheets

US 8,881,941 B2

EVAPORATOR DEVICE FOR VOLATILE SUBSTANCES

CROSS REFERENCE TO RELATED APPLICATION

The present invention is based on and claims priority to Provisional Application No. 60/863,051 which was filed Oct. 26, 2006, the contents of which are specifically incorporated by reference herein.

BACKGROUND

1. Field of the Disclosure

The present invention relates in general to a device for evaporating volatile or active substances. The active substances may be contained for instance in a tablet, or a tray-shaped container provided with a membrane.

In particular, a first object of the invention refers to an evaporator device for volatile substances, provided with a closure system that facilitates the replacement of the refill or container of the volatile substance.

It is also an object of the present invention to provide a safety closure system for the evaporator device, which makes difficult for children to get access to the tablet or container of the volatile substance.

2. Related Art

Evaporator devices for volatile substances are very well-know. Some of them incorporate a bottle containing an active substances and a wick immersed in part inside said bottle. Other types of evaporator devices use tablets impregnated with the volatile substance, or containers closed by a semi-permeable membrane through which a substance in the container can evaporate.

These evaporator devices incorporate means, which allow the replacement of the bottle or container when the volatile substance has been consumed.

SUMMARY

The invention refers to an evaporator device for volatile substances comprising heating means to evaporate a volatile substance from a cartridge, where the cartridge needs to be introduced completely in the device by sliding.

The invention provides a closure system for a volatile substance evaporator such an air freshener, an insecticide, a biocide, a descongestioning formulae, etc., which preferably is provided with a child-proof mechanism. The device of the invention prevents accidental contact between the liquid and uncontrolled actors (children, pets, etc). For that purpose, the closure system involves:

a two steps manipulation procedure requiring the use of the two hands

More in particular, the invention provides an evaporator device for volatile substances which comprises a casing including an internal chamber, and an aperture providing access to said chamber. A tablet or container of volatile substances is housed within said chamber.

A movable closure member is provided in said casing for closing and opening said aperture, wherein the closure member and the container are associated in such a manner, that during the opening movement of the closure member, at least part of the container is extracted out of the chamber. In this manner, when the closure member is opened by the user, the refill or container is extracted so that for the user is very simple to get access with its fingers to the container, which was previously housed within said chamber.

Some advantages of the invention are:

increased probability that the refill is not accessible if the container is not correctly opened, thereby reducing the risk of a child getting in contact with the volatile substance.

the space required for housing the refill is reduced (no extended part out of the heating area).

BRIEF DESCRIPTION OF THE DRAWINGS

To complete the description that is being made and with the object of assisting in a better understanding of the characteristics of the invention, in accordance with a preferred example of practical embodiment thereof, attached as an integral part of said description, is a set of drawings wherein by way of illustration and not restrictively, the following has been represented.

DESCRIPTION OF THE EMBODIMENTS

Figure 1:
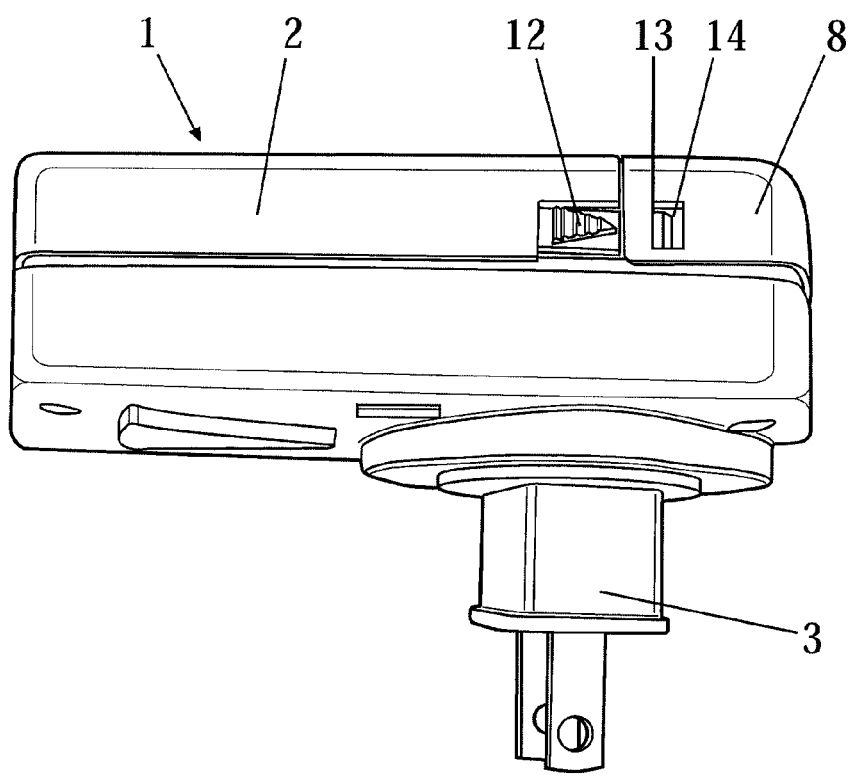
FIG. 1.—shows a perspective view of the device in a horizontal position when the closure member is locked.

In the attached figures it can be observed that the evaporator device (1) of the invention, comprises a casing (2) provided conventionally with an electric plug (3) for its connection to an electric socket to power a PTC heating resistor (not shown), which generates heat for the evaporation of a volatile or active substance.

In this preferred embodiment, the volatile substance is contained in a refill or tray-shaped container (4) provided with a semi-permeable membrane at one of its faces. The volatile substance may be for instance a liquid or a gel.

The casing (2) incorporates internally a chamber (5) adapted in size and shape to receive said container (4). The chamber (5) can be accessed through an aperture (7) provided at one of the ends of the casing (2).

The casing (2) has a rectangular prismatic shape, and in its normal use is located vertically, so that the closure member (8) is located in the lower end of the casing.

The container (4) of volatile substances can be housed within the chamber (5) in a sliding manner, for that the container (5) incorporates lateral rails (6,6').

Figure 2:
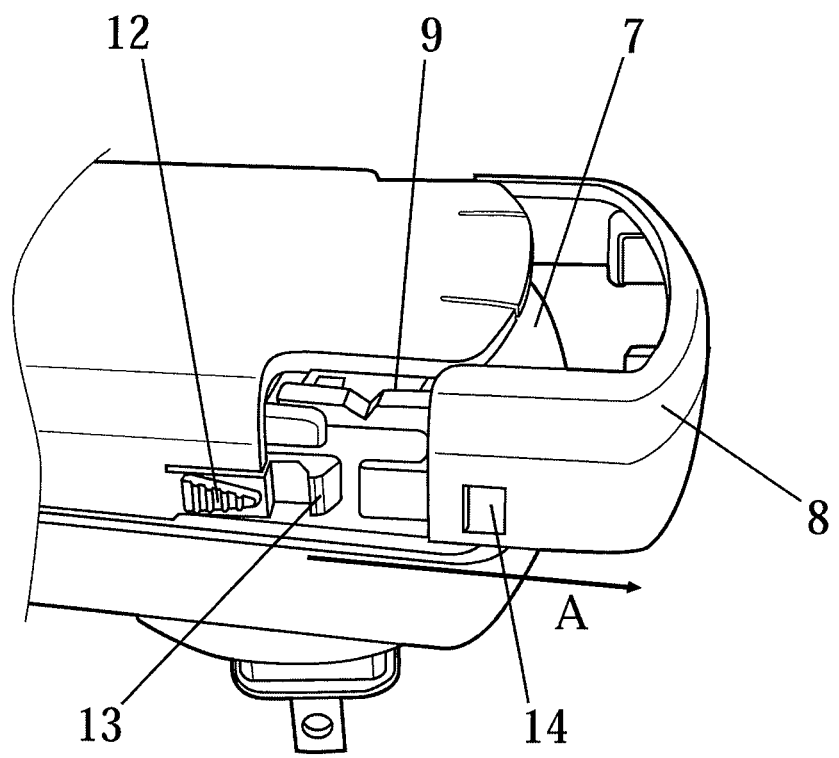
FIG. 2.—shows a perspective view of the device in a first stage of the opening displacement of the movable closure member.
Figure 3:
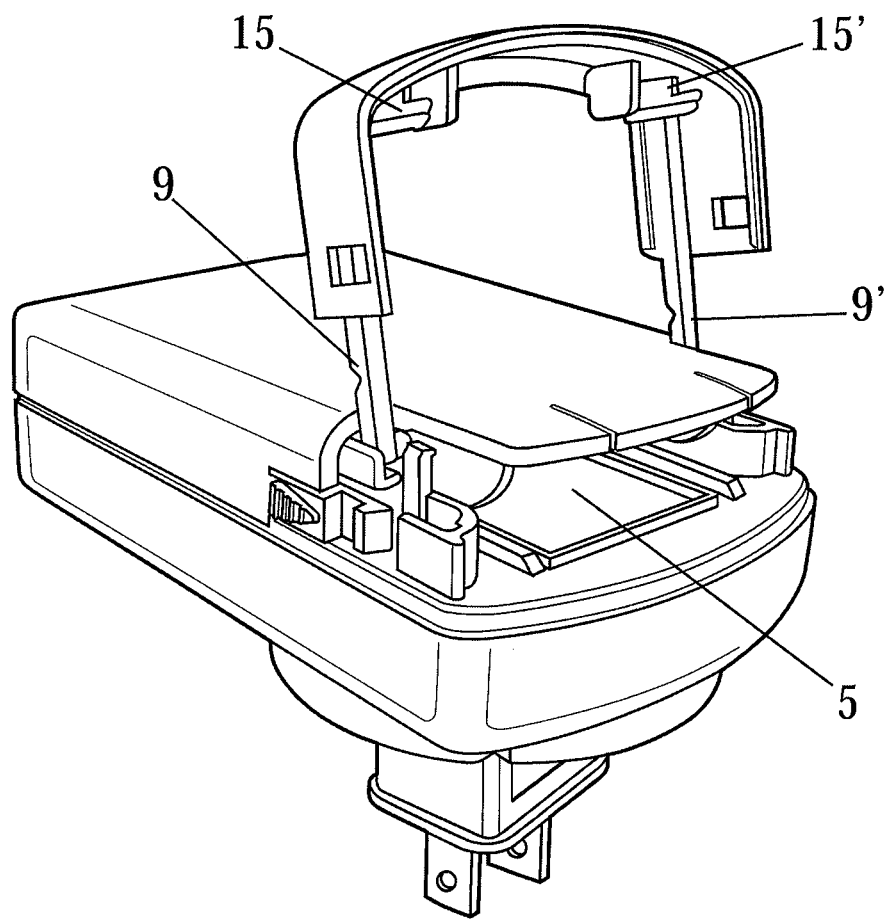
FIG. 3.—shows another perspective view of the device in a second stage of the opening displacement of the movable closure member.
Figure 4:
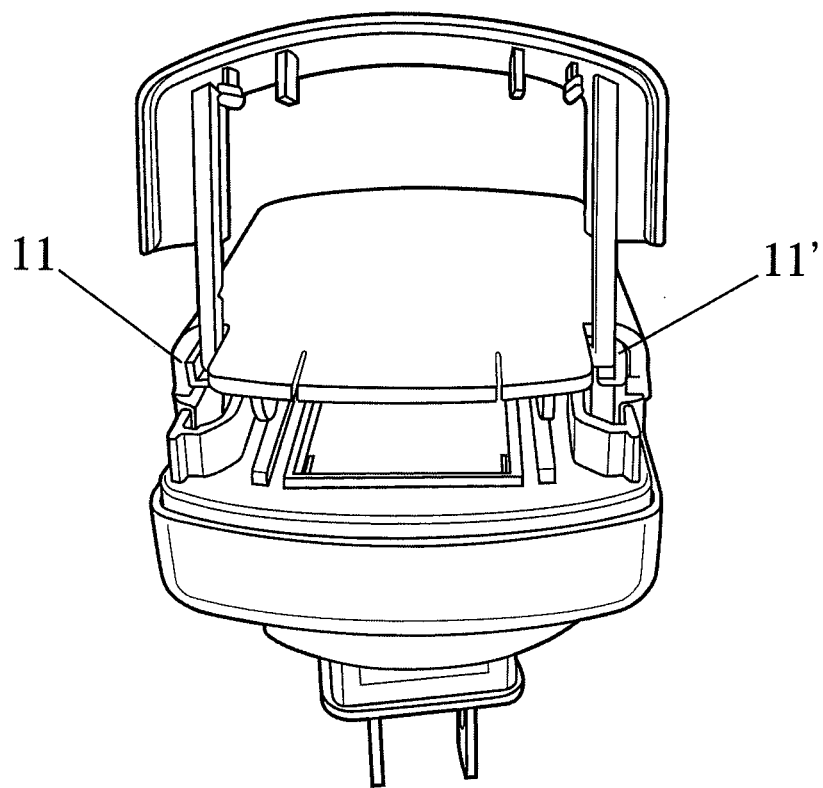
FIG. 4.—shows a front perspective view of the device.

A movable closure member (8) is provided in said casing (2) for closing and opening the aperture (7). The closure member (8) has two guiding arms (9,9'), having respectively pins (10,10') in their free ends, orthogonally located in respect to the guiding arms (9,9'). The guiding arms (9,9') are inserted inside the casing (2), and may slide along respective lateral guides (11,11') as shown in FIG. 4. The displacement of the closure member (8) during the opening operation of the same, consist of the combination of two movements. A first movement represented by arrow (A) in FIG. 2, in which the closure member moves on an horizontal plane defined by the prismatic shape of the casing (2). At the same time that the closure member is displaced in the direction of arrow (A), it can pivot about the pins (10,10') and moves upwards in the direction of arrow (B) in FIG. 6.

Preferably, the evaporation device of the invention incorporates safety means for the closure system, in order to make difficult for children to open the closure member, extract the container and get in contact with the volatile substance. In this preferred embodiment, the safety means comprises two flexible arms (12,12') having respectively teeth (13,13') at their free ends.

In turn, the closure member (8) has windows (14,14') arranged in such a manner that, in the locked position of the closure member (8), the teeth (13,13') seat inside the windows (14,14') as shown in FIG. 1.

In order to release the engagement between the teeth (13, 13') and the closure member (8), the user must pressure simultaneously the flexible arms (12,12') until the teeth (13,13') are extracted from the windows (14, 14'). At the same time, the user needs to move the closure member (8) in the direction of arrow (A).

During the movement to close the aperture (7), the closure member (8) pressures the flexible arms (12,12') in their teeth (13,13') which are able to lock the closure member in a snap coupling.

The closing and opening operations of the closure member (8), can be carried out easily by an adult, but are difficult for children or pets, thereby preventing damages caused by the volatile substance.

Figure 5:
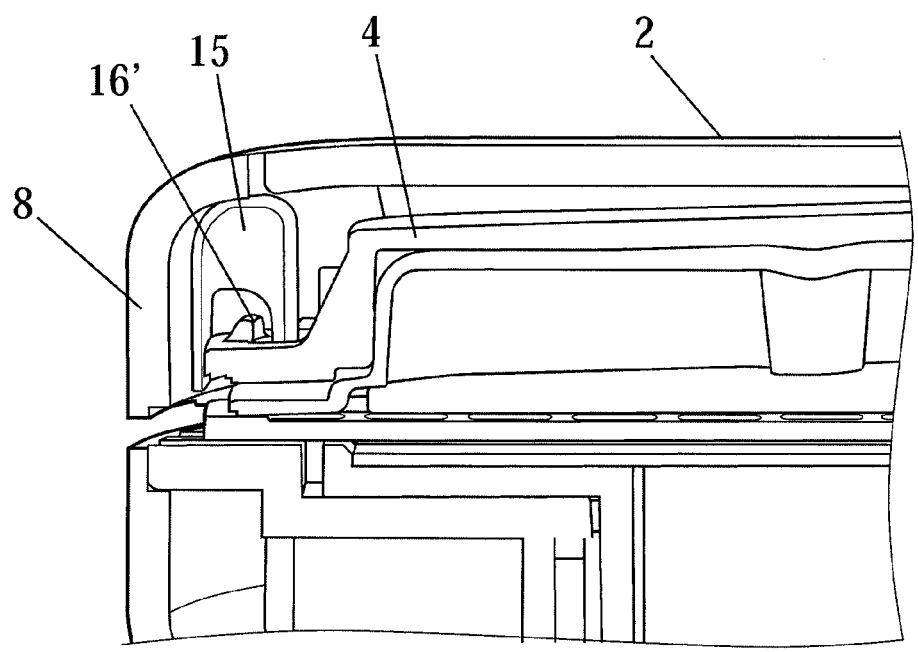
FIG. 5.—shows a cross-sectional view of a portion of the device in the closed position of the closure member, which is engaged with the refill or container.
Figure 6:
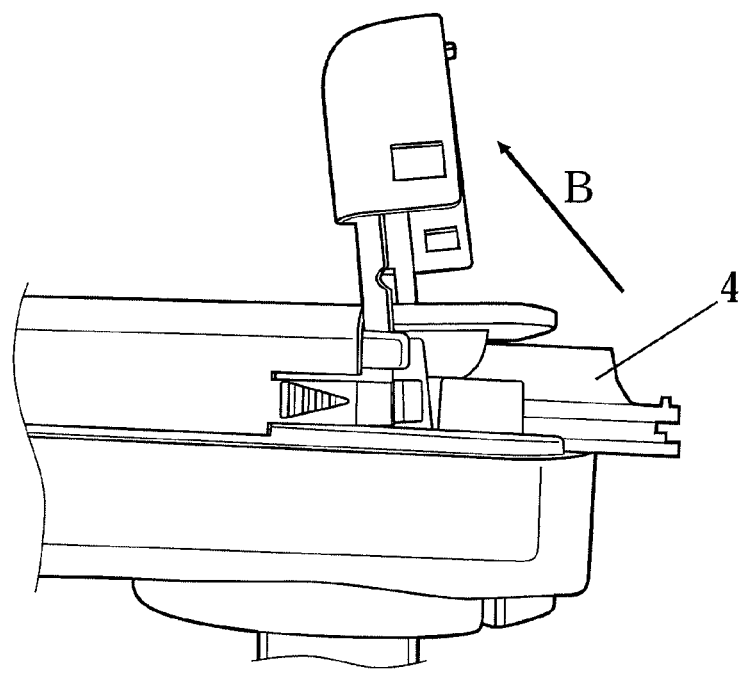
FIG. 6.—shows a perspective view of the device in a second stage of the opening displacement of the movable closure member, wherein the container has been partially extracted out of the casing of the device.
Figure 7:
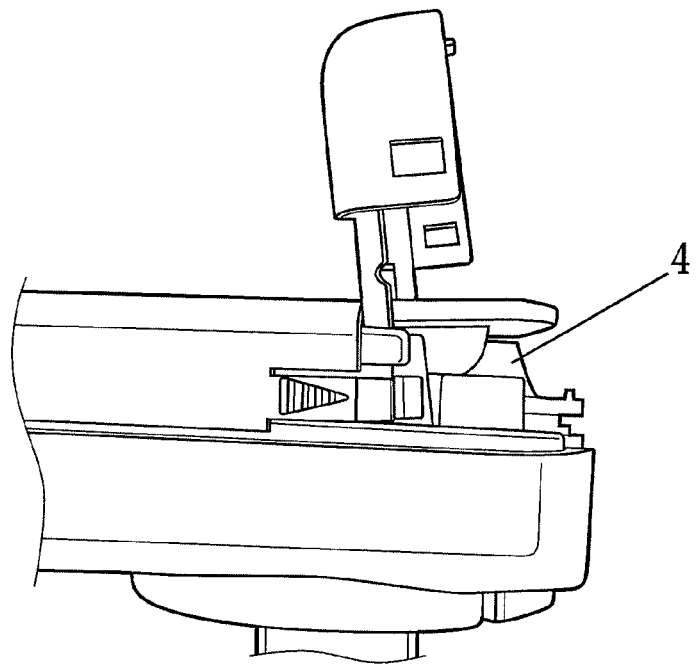
FIG. 7.—shows a perspective view of the device in a second stage of the opening displacement of the movable closure member, wherein the container has not been extracted from the device due to an incorrect aperture of the closure member.
Figure 8:
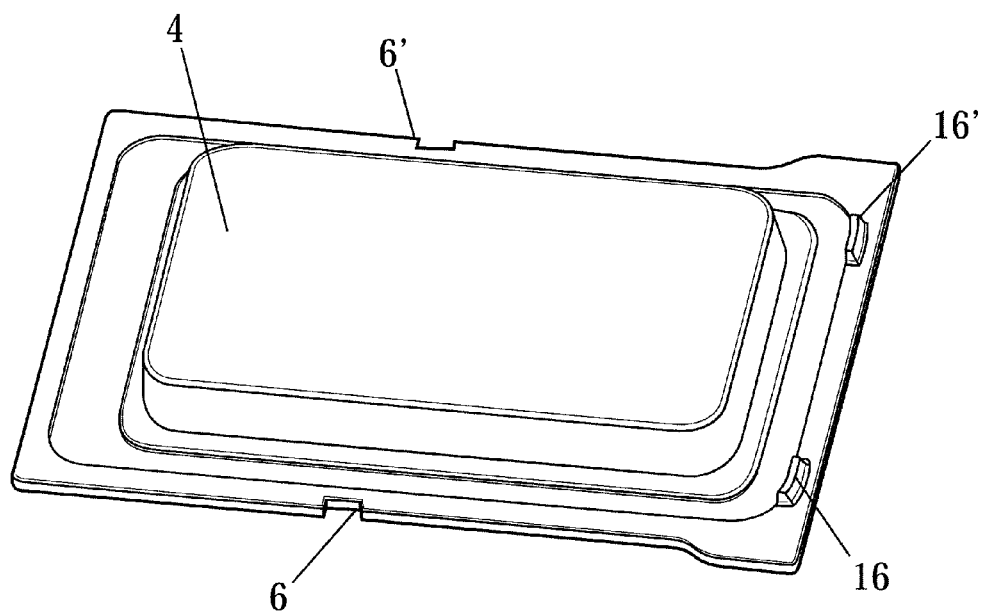
FIG. 8.—shows a perspective view of the refill or container of the volatile substances.
Figure 9:
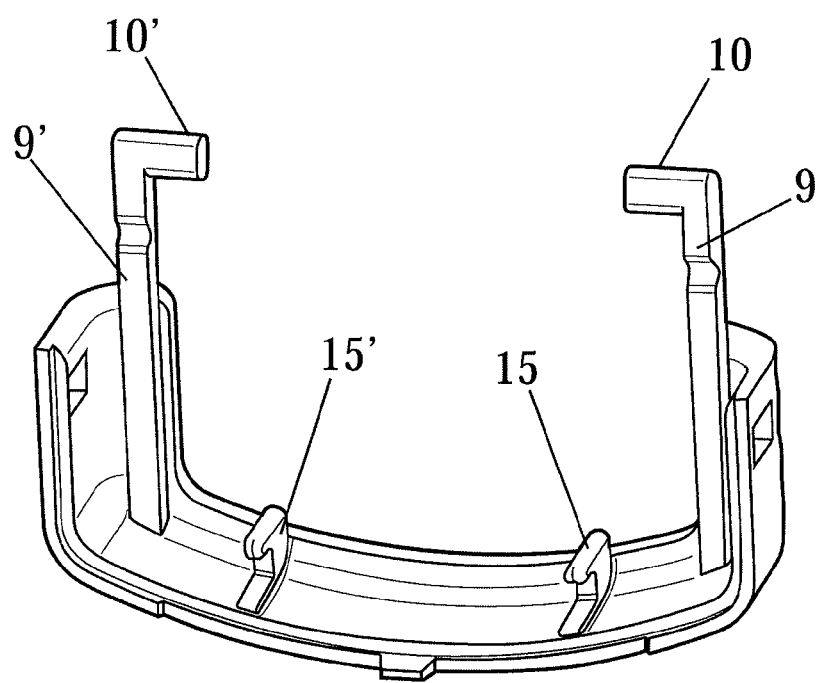
FIG. 9.—shows a perspective view from below of the closure member.

The closure member and the container are associated in such a manner that during the opening movement of the closure member, at least part of the container is extracted out of the chamber. For this operative association, the closure member (8) is provided internally with hooks (15,15'), and the container has walls (16,16'). As it can be observed in FIG. 5, when the closure member (8) is to be opened, the hooks (15,15') and the walls (16,16') are engaged, so that the movement of the closure member (8) pull the container out of the chamber (5). When the closure member (8) moves in the direction of arrow (B), said engagement between the hooks and the walls, is released. After this action, the container (5) is partially extracted from the chamber (7) as shown in FIG. 6, so that the user can get access to the container when it is necessary to replace the same by a new one after the consumption of the volatile substance.

What is claimed is:

1. Device for the evaporation of volatile substances comprising:
    a casing including an internal chamber and an aperture providing access to said chamber,
    a closure member coupled with said casing, said closure member being movable manually by the user with respect to the casing for closing and opening said aperture during the normal use of the device,
    a container of volatile substances housed within said chamber,
    wherein the closure member and the container are provided with co-operating engaging means, said engaging means configured so that the closure member engages the container during a first stage of an opening movement of the closure member to allow extraction of at least part of the container out of the chamber,
    the casing and the closure member are provided with a pair of co-operating releasable locking means, said means being configured so as to engage the closure member and the casing in a locked position, and to release said engagement by simultaneously pressing both locking means,
    the closure member is provided internally with hooks, and the container has walls so that the hooks and the walls are engaged when the closure member is to be opened, such that movement of the closure member pulls the container out of the chamber,
    and wherein the closure member pivots about pins in order to release engagement between the hooks and the walls.

2. Device according to claim 1 wherein the container of volatile substances is housed within the chamber in a sliding manner, for that the container incorporates lateral rails.

3. Device according to claim 1 wherein said co-operating releasable locking means comprises two flexible arms provided in the casing and windows provided in the closure member, said arms having respectively teeth at a free end of each of the arms, respectively, and windows arranged in such a manner that, in a locked position of the closure member, the teeth seat inside the windows.

4. Device according to claim 1 wherein the device further comprises heating means arranged in the casing for heating the volatile substance.

* * * * *